United States Patent [19]
Puri et al.

[11] Patent Number: 6,003,382
[45] Date of Patent: Dec. 21, 1999

[54] COMPUTER CONTROL SHEAR CELL TESTER

[75] Inventors: Virendra M. Puri, State College; Dauda D. Ladipo, Boalsburg, both of Pa.

[73] Assignee: The Penn State Research Foundation, University Park, Pa.

[21] Appl. No.: 09/104,650

[22] Filed: Jun. 25, 1998

Related U.S. Application Data

[60] Provisional application No. 60/050,668, Jun. 25, 1997.

[51] Int. Cl.$^6$ .................................................. G01N 3/24
[52] U.S. Cl. ............................................. 73/841; 73/815
[58] Field of Search ............................ 73/815, 841, 842, 73/843, 844, 845, 846

[56] References Cited

U.S. PATENT DOCUMENTS

| | | | |
|---|---|---|---|
| 3,930,701 | 1/1976 | Peschl | 73/843 |
| 4,633,712 | 1/1987 | Scieszka | 73/866 |
| 4,825,700 | 5/1989 | Vardoulakis et al. | 73/749 |
| 5,456,118 | 10/1995 | Hines et al. | 73/818 |
| 5,606,133 | 2/1997 | Hines et al. | 73/824 |
| 5,712,431 | 1/1998 | Vilendrer | 73/841 |

OTHER PUBLICATIONS

Kamath, S., "Flow properties of powders using four testers–measurement, comparison and assessment," Powder Technol, pp. 277–289, (1993).
Jenike, A. W., "Gravity flow of bulk solids," Bulletin 108, Eng. Expt. , Sta. Univ. of Utah (Salt Lake City, Utah.), vol. 52 (No. 29), pp. i–v,viii,i, (1961).
Peschl, I. A. S. Z.,, New developments in the field of shear test equipment and their application in industry, International Symposium Powder Technology (Kyoto, Japan.), pp. 150–164, (1981).
Schwedes, J., "Measurement of flow properties of bulk solids," Proceedings of the First International Particle Technology Forum. Part III, pp. 3–10, (1994).
Kamath, S., "Measurement of powder flow constitutive model parameters using cubical triaxial tester," Powder Technology, pp. 59–70, (1997).
Tsunakawa, H., "Measurement of the failure properties of granular materials and cohesive powders," Powder Technol, No. 33, pp. 249–256, (1982).
Miyanami, K., "Direct shear test of powder beds," Kona, No. 1, pp. 29–39, (1983).
Haaker, C., "A constant volume shear tester–development and experience," Bulk Solids Handling, vol. 13 (No. 1), pp. 129–133, (1993).
Schwedes, J., "Measurement of powder properties for hopper design," Journal of Engineering for Industry, pp. 55–59, (1973).
Williams, J. C., "The comparison of the failure measurements of powders with theory," Powder Technol, No. 1, pp. 199–206, (1967).
Standard Testing Technique for Particulate Solids Using the Jenike Shear Cell Institute of Chemical Engineers. Warwickshire, UK. (1989).
Annual Book of ASTM Standards vol.: 40.8, Philadelphia, PA (1995) Ladipo, D., "Computer controlled shear cell for particulate materials and shear plane formation analysis," Master Thesis, The Pennsylvania State University, p. 60, (Dec. 1995).

(List continued on next page.)

Primary Examiner—Max Noori
Attorney, Agent, or Firm—Thomas J. Monahan

[57] ABSTRACT

A computer controlled shear cell (CCSC) tester for bulk solids, especially powders, that allows the determination of a Yield Locus curve from a single test procedure. The principle of the CCSC is that yield states can be maintained in a test cell over a range of normal and shear stresses in the same test. This leads directly to a Yield Locus curve. With its flexible design, the CCSC can also be used as a Jenike shear cell or a direct shear cell. Use of the CCSC allows the testing time and amount of material needed for testing to be reduced as compared to current testing methods.

22 Claims, 18 Drawing Sheets

OTHER PUBLICATIONS

Arnold, P. C., "On the machine dependence of flow property measurement s on bulk solids," Bulk Solids Handling, No. 7, pp. 397–400, (1987).

Desai, C. S., "Constitutive laws for engineering materials with emphasis on geologic materials," Prentice–Hall, Inc., p. 283, (1984).

Kamath, S., "Comparison of test methods for measuring bulk flow properties of wheat flour and sugar," M S Thesis, The Pennsylvania State University, pp. 58–62, (1992).

Duffy, S. P., "Evaluation of the computer controlled dynamic yield locus tester," M S Thesis, The Pennsylvania State University, pp. iii, 75–77, (1997).

Akers, R.J., "The certification of a limestone powder for Jenike testing: CRM 116. Bureau of Common Reference (BCR)," Commission of the European Communities (Luxembourg), p. 2, (1992).

COMPUTER CONTROL SHEAR CELL TESTER

This application claims priority to U.S. Provisional Application No. 60/050,668 filed Jun. 25, 1997.

BACKGROUND

In handling and storing bulk solids, many applications of tableting, particle size reduction, mixing, packaging and quality control require that bulk solid handling systems be designed to precise engineering specifications to ensure a reliable handling system. To design a reliable handling system, it is necessary to characterize the flow properties of the bulk solid to be used in the system. It is known to use a Yield Locus plot to evaluate the flow properties of bulk solids, especially powders. The Yield Locus is the plotting of an averaged straight line which is the average of several plotted points on a shear stress vs. normal stress plot. The plotted points of the Yield Locus represent different normal load stress states of material samples having the same initial bulk density and testing conditions.

Shear tests are common in powder technology to characterize the flowability of granular materials and powders. Several shear testers and procedures have been used to measure the flow properties of powders. Some of the commonly used testers are the Jenike shear cell, the direct shear box, the rotational shear cell, and the biaxial tester. Each tester has its own specific problems, but most of the testers mentioned require laborious test procedures and separate tests to obtain each point to be plotted on the Yield Locus plot. It has been found that no single tester is suitable for reliably testing all bulk solid materials.

The Jenike shear cell tester is the more widely used tester in industry. The Jenike tester is usually made up of an upper ring, lower ring, a base, a mold ring and a lid. The lower ring is fixed to the base and the upper ring is placed on top of the lower ring to form a shear cell. The molding ring removably interlocks on top of upper ring. The lid fits from above into the openings of the molding ring and upper ring. Tests with the Jenike tester are normally performed in two main stages. In the first stage, the shear cell is careful filled above the top of upper ring with the material to be tested. The molding ring retains the material that would normally flow over the top of the upper ring. The lid is then placed into the opening of the molding ring. Next, the material is initially compressed or consolidated by twisting the lid while applying a static axial load downward on the lid that is normal to the cell. After the initial consolidation, the axial load, lid and molding ring are removed. Any remaining powder the extends above the upper ring is scrapped away. Next, the lid is place back into the upper ring with the axial load. The axial load on the lid creates a vertical consolidation stress $\sigma_{pr}$, also referred to as normal stress or normal load. The material is then forced to shear by horizontal displacement of the upper ring over the lower ring until a steady state failure condition is reached. A load cell is connected to whatever mechanism is employed to displace the upper ring. The load cell is used for measuring the shear stress $T_{pr}$. The steady state failure is marked by the shear stress $T_{pr}$, remaining constant. After reaching the steady state failure, the vertical normal stress is reduced to zero and the lid is retracted. In the second stage, a vertical normal stress of $\sigma_s$ is applied to the lid, whereby the value of $\sigma_s$ is less than the value of $\sigma_{pr}$. The material is again forced to shear by horizontal displacement of the upper ring over the lower ring until the material shears to failure. The shear to failure this time is marked by the shear stress passing through a maximum value followed by a reduction in value. This maximum stress value from the second stage is one point to be plotted on the Yield Locus plot. In order to measure other points for the Yield Locus, the two stages must be repeated. When the stages are repeated for each point, a new unconsolidated sample of material must be loaded into the cell, whereby the same value of $\sigma_{pr}$ must be obtained, but a different value of $\sigma_s$ is applied for each point. As is evident, it is necessary to use a large amount of test material which may not be readily available in order to obtain a Yield Locus plot. Also, it is very difficult to reproduce the exact consolidation of the material to get the same value for $\sigma_{pr}$ and therefore a margin of error exists in the testing of a material.

There has also been some work done towards making test procedures simpler and faster with the development of testers which measure the Yield Locus from a single test. Such testers have been referred to as "constant volume" testers. However, published results either do not include comparisons with accepted standards, or the methods published still involve complicated test procedures. Therefore, there is a definite need to improve upon available testers and test procedures.

It is an object of the present invention to provide tester for bulk solids, especially powders, with which the Yield Locus data can be obtained directly from a single test using a simplified testing procedure.

It is another object of the present invention to provide a tester and a simplified testing procedure for reducing the amount of material needed to be tested in order to obtain a Yield Locus plot.

SUMMARY OF THE INVENTION

The present invention is a Computer Control Shear Cell (CCSC) tester and a single test procedure using the CCSC. The CCSC tester includes a lower measuring device for measuring load; a movable ring platform connected to and movable along the lower measuring device; a lower ring mounted to an upper surface of the movable ring platform; a fixed ring platform supported above the lower ring and movable ring platform; an upper ring mounted to a lower surface of the fixed ring platform and above the lower ring; a lid; a lid opening in the fixed ring platform to allow access to the upper ring; a lid movement apparatus connected to the lid to move the lid and apply a load to the lid; an upper measuring device connected to the lid movement device to measure the load applied to the lid; an actuator connected to the movable ring platform for moving the movable ring platform along the lower measuring device; and an actuator measuring device connected to the actuator to measure load experienced by the actuator during movement of the movable ring platform. The single test procedure includes the steps of aligning an upper ring with a lower ring to form a shear cell; loading a test material into the shear cell; placing a lid into the upper ring to initially consolidate the test material; twisting the lid while applying a normal load to the lid until the test material is critically consolidated; displacing the lower ring in relationship to the upper ring while applying the normal load to the lid; measuring the load due to shear stress of the material as the lower ring is displaced; displacing the lower ring until a steady state failure condition is reached, the steady state failure marked by shear stress $T_{pr}$, remaining constant; decreasing the normal load slowly after the steady state failure condition has been reached; and continuously recording normal load values and shear stress values of the test material as the normal load is reduced. The CCSC is unique as it uses computer control to automate the tester and test procedure.

DETAILED DESCRIPTION

Figure 1:
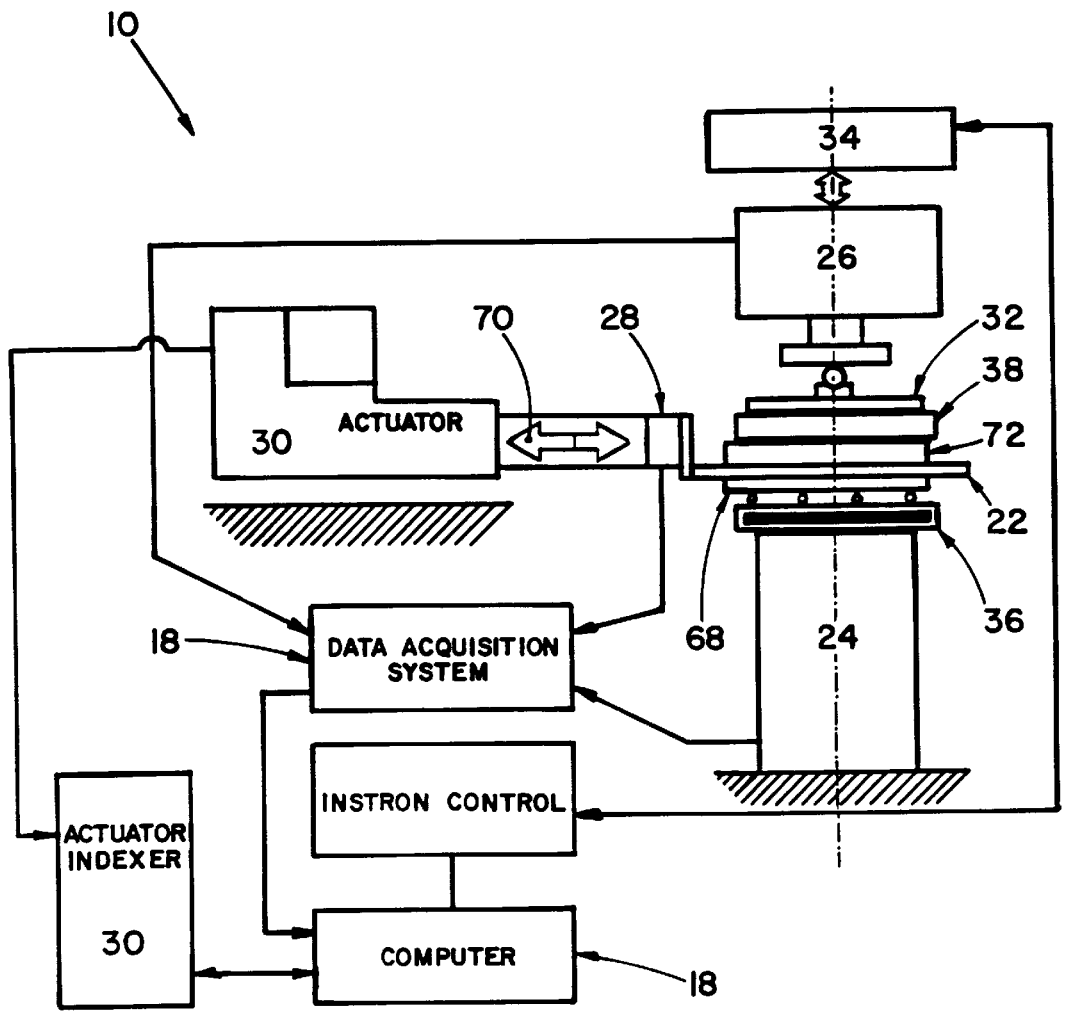
FIG. 1 is a schematic of a Computer Control Shear Cell (CCSC) according to the present invention.
Figure 2:
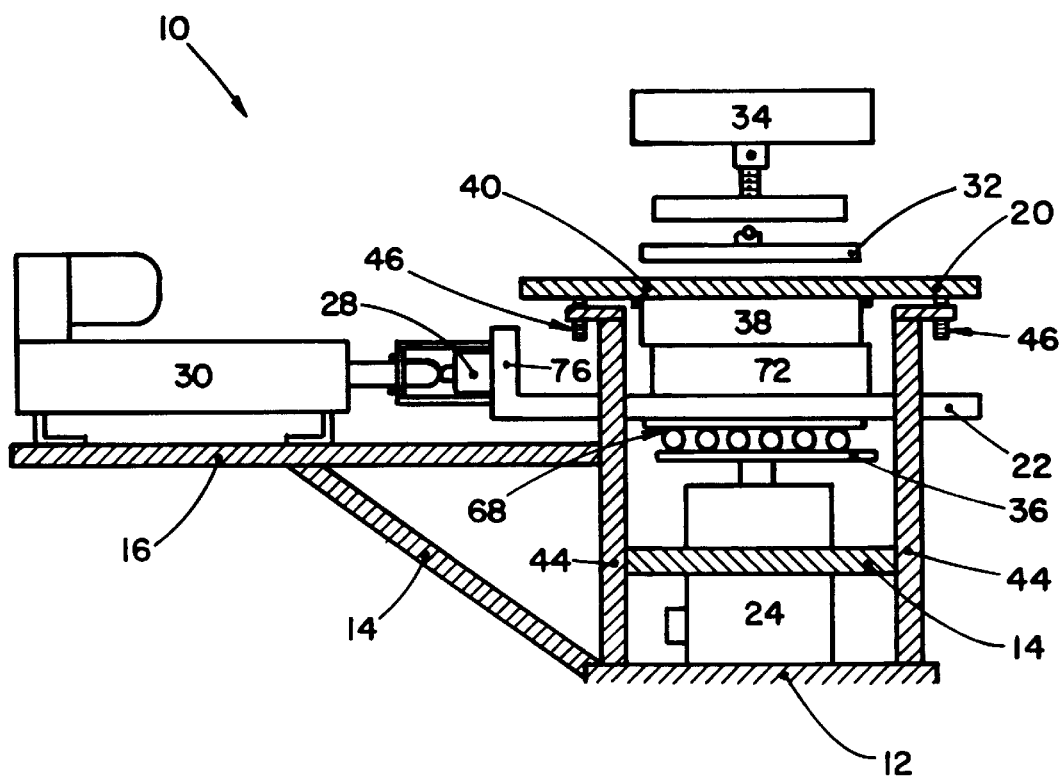
FIG. 2 is a schematic of the CCSC prototype according to the present invention.

The present invention is a Computer Control Shear Cell (CCSC). The CCSC is a tester that includes the features of computer control and the flexibility to additionally function as a Jenike or Direct shear cell tester. Both of these features are not included in the current "constant volume" testers. A system schematic of the CCSC 10 is shown in FIG. 1. FIG. 2 shows a schematic of the mechanical apparatus used in a prototype of the CCSC 10. In order to differentiate between the Yield Locus plot obtained using a Jenike shear cell and the CCSC, the Yield Locus plot obtained using the CCSC will be referred to as a curve instead of the averaged straight line. This is because the Yield Locus plot obtained using the CCSC is actually a curve instead of the averaged straight line normally obtained. The use of the term curve will always referred to a plot obtained using the continuously changing strain controlled normal load of the CCSC, as opposed to a plot obtained using the Jenike shear cell procedure.

Figure 3:
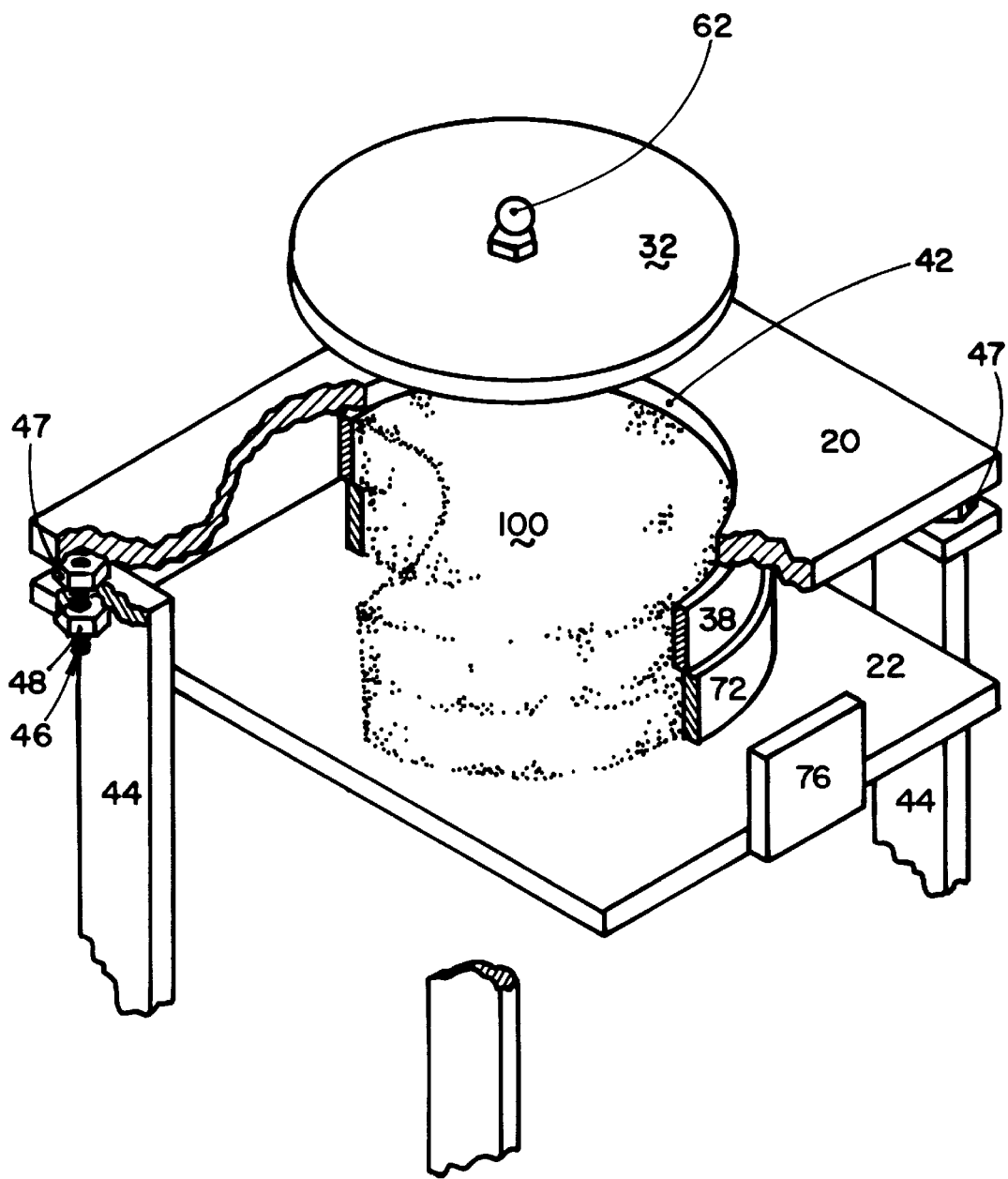
FIG. 3 is a perspective cutaway view of one method of attaching a fixed ring platform of the CCSC according to the present invention.
Figure 4:
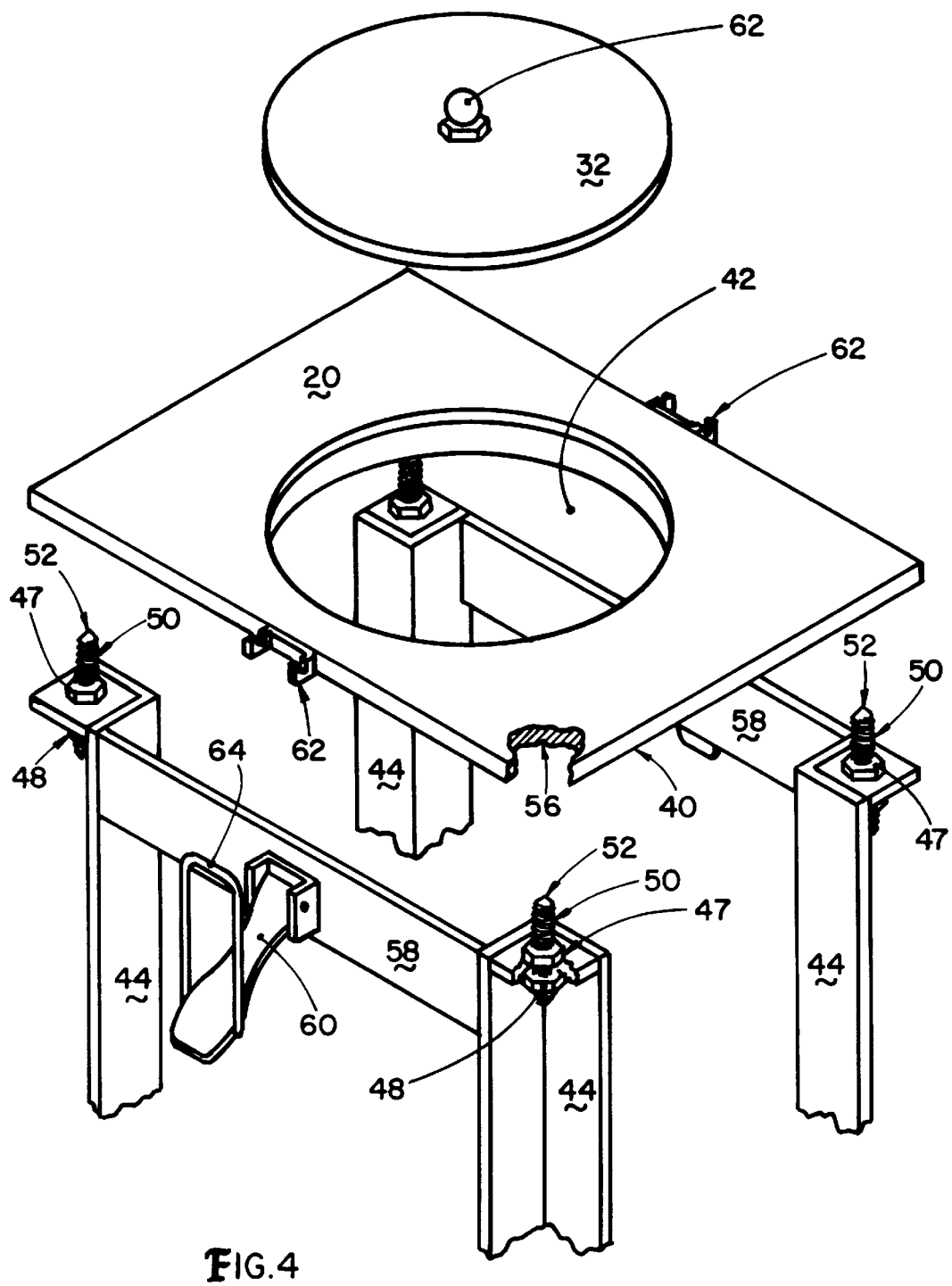
FIG. 4 is a perspective cutaway view of another method of attaching a fixed ring platform of the CCSC according to the present invention.

As shown in FIGS. 1–4, the main components of the CCSC 10 are supported by a framework. The framework shown includes a main base 12, structural supports 14, and an actuator base 16. The structural supports 14 can be of any orientation and therefore the framework can be of any orientation, so long as support is provided for the main components. The main components are a computer system 18, fixed ring platform 20, movable ring platform 22, lower load cell 24, upper load cell 26, actuator load cell 28, actuator 30, lid 32 and lid movement apparatus 34. The fixed ring platform 20 is supported over the lower load cell 24. The lower load cell 24 is mounted to the main base 12. The lower load cell 24 includes a load cell platform 36. The fixed ring platform 20 includes an upper ring 38 mounted to a lower surface 40 of the fixed ring platform 20. The upper ring 38 is shown as part of the platform 20, but could be movably attached (not shown) to allow adjustment and alignment of the ring 38. The fixed ring platform 20 includes a platform opening 42 to receive the lid 32. The platform opening 42 could also be sized to accept a molding ring (not shown) and the lid 32 would then fit into the molding ring, similar to the Jenike tester. The fixed ring platform 20 is shown in FIG. 3 mounted to four supports 44 using studs 46 extending from the platform 20 and nuts 47, 48. Nut 47 allows for the adjustment in height of the fixed ring platform 20. FIG. 4 shows another arrangement of mounting the fixed ring platform 20 to the supports 44. FIG. 4 shows studs 50 that include pointed tipped heads 52. The fixed ring platform 20 includes indentations 54 on the lower surface 40 of the platform 20 to receive the pointed tipped heads 52. Additionally, side supports 58 are included to accepted the mounting of lock down latches 60 and the fixed ring platform 20 includes catches 62. The latches 60 include hooks 64 that interconnect with the catches 62 to lock down the platform 20 on the pointed head studs 50. By adjusting the height of the pointed heads 52 using nuts 47, 48, the height of the fixed ring platform 20 above the other components can be adjusted. This arrangement allows easier attachment and adjustment of fixed ring platform height. The lid opening 42 is at least the size of the inside diameter of the upper ring 38 to allow placement of the lid 32 into the upper ring 38. The lid 32 is connected to the lid movement apparatus 34. The lid movement apparatus 34 moves the lid 32 in and out of the upper ring 38 and applies the load to the lid 32. The lid movement apparatus 34 allows the lid 32 to be twisted by hand and includes an upper load cell 26 to measure the load applied to the lid 32. The lid 32 is shown with a ball like handle 62 which is connected to the lid movement apparatus 34, whereby the lid 32 rotates about the handle 62. The lid movement apparatus 34 can be almost any device available which allows control of a load applied to the lid 32 and allows recording of the load value applied to the lid 32. The lid movement apparatus 34 can be separate from the framework or part of the framework. The movable ring platform 22 is mounted to the load cell platform 36 using a roller bearing mechanism 68 to allow movement of the platform 22 along the load cell platform 36 in the directions indicated by arrows 70. The roller bearing mechanism 68 can be substituted by any known method of movably mounting the movable ring platform 22 to the load cell platform 36. The movable ring platform 22 includes a lower ring 72 mounted on an upper surface 74 and an arm 76 extending upward on end of the platform 22. The lower ring 72 is shown as part of the platform 22, but could be movably attached (not shown) to allow adjustment and alignment of the ring 72. The actuator base 16 is mounted along the framework so that an actuator 30 is connected to the arm 76 of the movable ring platform 22. The connection of the actuator base 16 to the framework is not necessary for the CCSC to function. An actuator load cell 28 is mounted between the actuator and the arm 76 to measure the shear stress during testing.

The present invention provides a single test procedure having four stages using the CCSC. The single test procedure is described with reference to the above-mentioned apparatus, but could be employed with other apparatus configured for the procedure. The first stage is to form a cell by placing the upper and lower rings 38, 72 in contact with each other. The upper and lower rings 38, 72 are to be aligned as rings would normally be aligned for the Jenike shear cell. Then, the test material 100 is loaded into the cell formed by the upper and lower rings 38, 72 through the lid opening 42. In the case of powder, the test material 100 would be layered into the cell by sprinkling to increase the consolidation of the material.

In the second stage, the lid 32 is placed into the upper ring 38 by passing the lid 32 through the lid opening 42. Placement of the lid 32 is performed by the lid movement apparatus 34. During the second stage, the lid 32 is twisted while an axial load is applied by the lid movement apparatus 34 until the test material is critically consolidated. Critically consolidated is defined as the time where the normal load value applied to the material by the lid 32 no longer increases or decreases after another twist of the lid 32.

In the third stage, the actuator 30 displaces the lower ring 72 in relationship to the upper ring 38 by the pulling or pushing on the movable ring platform 22 in one of the directions shown by arrows 70. The lower ring 72 moves due to the roller bearing mechanism 68 between the movable ring platform 22 and the load cell platform 36. While the actuator 30 is displacing the lower ring 72, a normal load is applied by the lid 32 using the lid movement apparatus 34. The material is caused to shear during movement of the lower ring 72 while the normal load is applied. The actuator load cell 28 measures the shear stress as the lower ring 72 is displaced. Displacement of the lower ring 72 is continued until the steady state failure condition is reached, which is marked by the shear stress $T_{pr}$, remaining constant.

In the fourth stage, the normal load on the lid 32 is decreased slowly after the steady state failure condition has been reached. The lid movement apparatus 34 allows the lid 32 to rise as and if the material dilates when the load is reduced. The values of shear stress and normal load are continuously recorded as the normal load is reduced. The normal load record is the averaged load from the values recorded from the upper and lower load cells 26, 24. Each recorded shear stress value is then plotted against each normal load value at the time the shear stress value was recorded. This plot of the shear stress and normal load values produces the Yield Locus curve instead of the individual points produced using the Jenike shear cell procedure. The computer system 18 is used to control the actuator 30 and lid movement apparatus 34. The computer system 18 records the outputs from the three load cells 24, 26, 28, records load values applied to the lid 32, plots the points of the Yield Locus curve and monitors the testing procedure. The computer system 18 is programmed to automate the above-mentioned stages and automatically make the adjustments to the testing procedure as needed.

The Jenike test procedure can be applied using the CCSC by performing stages 1–3 and changing the steps in stage 4. In stage 4, when the steady state failure condition is reached, the displacement of the lower ring 72 is stopped and the normal load is completely removed. Then, a chosen normal load is applied. The chosen normal load should be lower than the normal load value recorded at the steady state failure condition, as is normally followed for the Jenike test procedure. When the chosen normal load is applied, displacement of the lower ring 72 is continued until a maximum shear stress value is reached. That shear stress value is plotted against the chosen normal load. As the conventional Jenike test procedure, all four stages must be repeated using new test material for each additional point to be plotted on the Yield Locus plot. After the points have been plotted, an averaged line is calculated to produce the Yield Locus.

For the prototype of FIGS. 1–4, a HP 3852A Data Acquisition System (DAS) and an IBM 486 computer were both part of the computer system 18 that provided control of the CCSC 10. The computer system 18 monitors the testing procedure and controls the main components of the CCSC 10. A Warner Electric linear actuator controlled by a Superior Electric PAC440 programmable indexer was used as the actuator 30 to provide displacement of the lower ring 72 for the shearing of the test material. The computer system 18 receives outputs values from the three load cells 24, 26, 28 and the indexer using the DAS. Displacement rates used for controlling the actuator 30 to cause shear were typically on the order of 1 mm/min. Since a high degree of control is required for applying the normal force, an Instron 4501 universal testing machine (UTM) was used as the lid movement apparatus 34. The UTM has a sensitivity of 0.001 mm/min for movement of the lid, a minimum axial force of 0.001 N that can be applied to the lid and a rated accuracy of 0.1% of full scale load.

Figure 5:
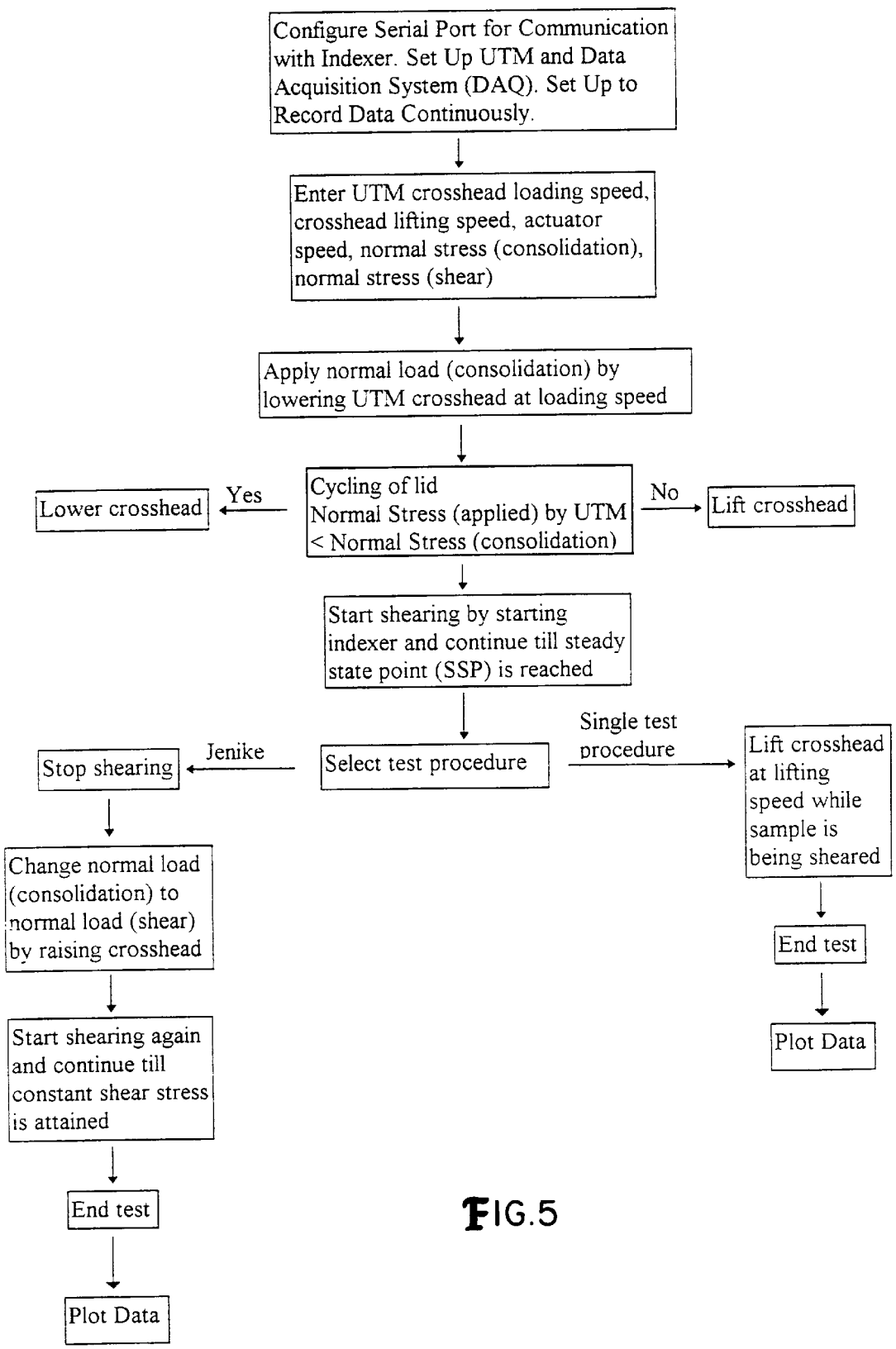
FIG. 5 is a flow chart of a computer program used with the CCSC prototype according to the present invention.

The computer program for control and data acquisition of the CCSC prototype was written in GWBASIC language. A flow chart of the program is shown in FIG. 5. The program of the CCSC computer system 18 programs the Superior Electric programmable indexer in RS274D language via a serial port. The indexer programming from the computer system 18 is stored in the indexer's non-volatile memory. The CCSC computer program sends an appropriate command string to the indexer during a shear test to control the movement of the actuator. The control system of the UTM and the DAS both operate in HPBASIC language. For the computer system 18 to communicate with the UTM, it was necessary to embed character strings written in HPBASIC code into the GWBASIC computer program of the prototype. The HPBASIC command strings were transmitted to the UTM and DAS through a general purpose interface bus.

For testing of the CCSC prototype, "all purpose" wheat flour and granulated sugar were used as test materials. They were chosen because both are inexpensive, readily available and of great importance to the food industry. Also, they are examples of cohesive and easy flowing particulate food materials, respectively. Also, shear test data is published for these powders that allows the comparison of results obtained from the CCSC prototype. Table 1 shows known load values and ranges for both test materials from Kamath, S., et al., *Flow properties of powders using four testers— measurement, comparison and assessment. Powder Technol.*, 76: 277–289, 1993.

TABLE 1

Shear test parameters

| Material | Consolidation stress (kPa) | Normal stress (kPa) | Replications |
|---|---|---|---|
| Wheat flour | 13.6 | 5.0, 8.0, 11.0 | 3 each |
|  | 27.3 | 10.0, 16.0, 22.0 | 3 each |
| Granulated sugar | 24.2 | 7.8, 11.8, 17.7 | 3 each |
|  | 30.9 | 11.8, 18.7, 23.6 | 3 each |

These load values were used in the testing of the single test procedure and the Jenike procedure using the CCSC prototype for comparison of results with known values produced by the conventional Jenike tester.

Testing of the CCSC was performed in a climate controlled laboratory at 23±1° C. and 60±10% relative humidity. The particle size distribution of the flour and granulated sugar were determined using a Leeds and Northrup MICROTRAC SRA particle size analyzer, Model 7995-11, in an isopropanol suspension. The flour and granulated sugar were stored in a refrigerated facility and equilibrated to laboratory temperature before testing. The moisture content of wheat flour and granulated sugar samples were 15±2.5% and 0.015±0.005% wet base, respectively, and the average (median) particle sizes were 61 μm and 539 μm, respectively.

Tests with the CCSC prototype were performed using above described four stage testing procedure and also using the Jenike procedure. The Jenike procedure was performed with the CCSC prototype by changing the fourth stage as described above. The procedure followed for the Jenike shear test using the CCSC was the conventional Jenike procedure as described in *Standard Testing Technique for Particulate Solids Using the Jenike Shear Cell*, Institute of Chemical Engineers. Warwickshire, UK, 1989. There were a few differences in Jenike procedure performed during testing as compared to the described conventional procedure. These differences are due to the configuration of the CCSC prototype. The main differences between a conventional Jenike test and the Jenike test using the CCSC prototype are as follows. The first main difference is that a normal load in the conventional test would be applied by weights and effectively static. However, using the CCSC prototype, the Instron cross-head that is part of the UTM is used to apply a cyclic load at a constant loading/unloading speed of 0.5–1.0 mm/min. A cyclic loading and unloading of force on the lid was required to keep the lid in contact with the test material without over loading the test material. Loading/unloading speed depends on the compressibility of the testing material and its rate of dilation or consolidation during the shearing of the material. A less compressible test material requires a lower speed than a more compressible test material. Lid movement during cycling of the load typically ranged between 0.005 and 0.015 mm for the CCSC prototype. The limiting factor in the displacement range is computer system, due to the frequency of measurement of test conditions and response by the computer system. In GWBASIC program language, the highest frequency measurement and response attainable was one set of measurements and response every second for the prototype.

Figure 6:
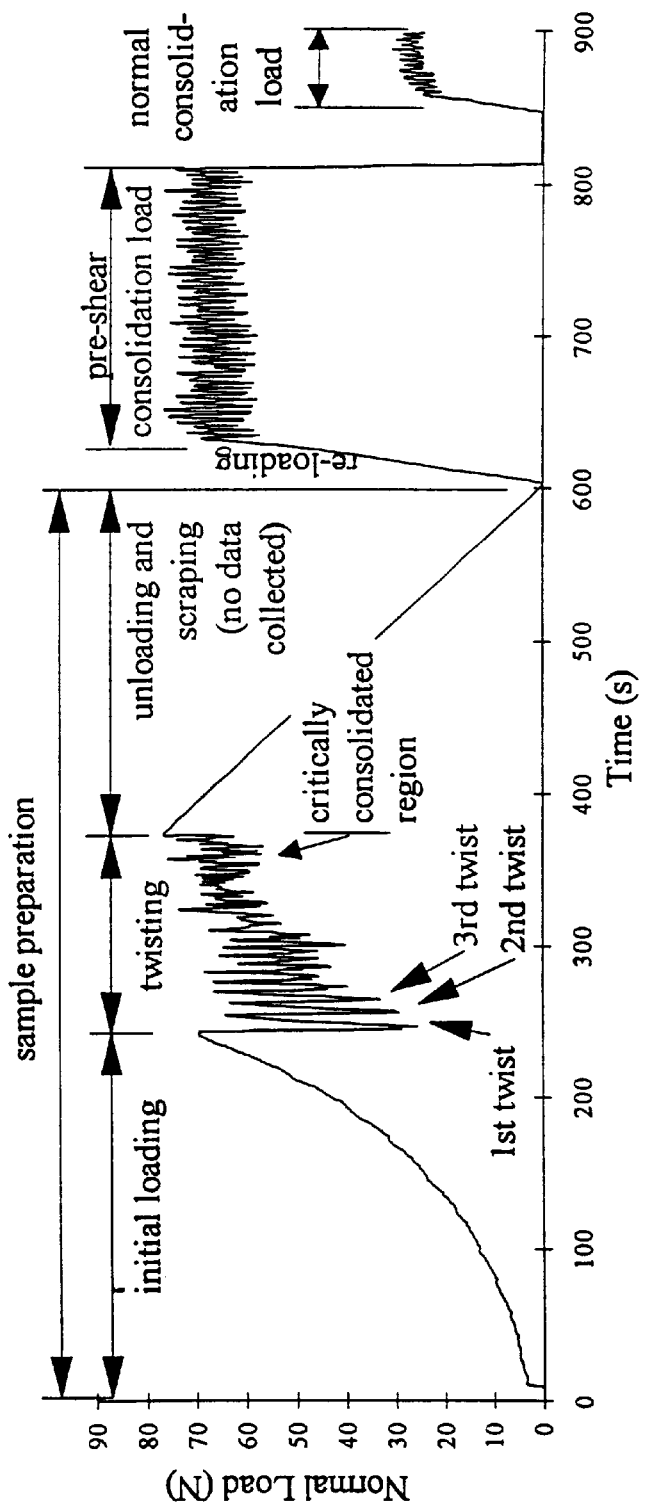
FIG. 6 is plot of recorded output data from the CCSC when used as a Jenike shear cell according to the present invention.

The second main difference is the procedure for twisting the lid 32 to obtain critical consolidation of the test material prior to shearing the material. The conventional Jenike test uses trial-and-error to determined the number of twists required. The CCSC 10 allows the consolidation progression to be monitored and the exact number of twists to be determined during the test. Determining the number of twists using the CCSC 10 is accomplished by observing the change in material response to a normal load during twisting, thus eliminating the need for trial and error. FIG. 6 shows a chart recorder output, as observed during a test and shows a plot of normal load against elapsed time, where the stages of the experiment are indicated. When the normal load reaches a specified pre-consolidation load value for a specific material, the lid 32 was given one twist, manually. The normal load value was provided to the computer system by the upper and lower load cells 26, 24. The specified pre-consolidation load values are published starting points for each specific test material. The initial effect of each twist using the CCSC prototype 10 was seen as a sudden drop in normal load as the material consolidated. Once the material consolidated, the normal load accumulated again, after which the lid 32 was given another twist. After a number of such twists, the normal load ceased to drop with further twisting. At this point the material was considered to be critically consolidated. The critical consolidation procedure using the CCSC 10 is automated by the computer program and requires no human interaction.

The third main difference is that the upper ring normally rests on the lower ring in the conventional Jenike apparatus. For testing using the CCSC 10, a gap of 0.75 mm was maintained between the upper ring and lower ring 38, 72. The gap eliminates contact by lower and upper rings 38, 72 and prevents energy loss during shearing of the test material. Energy loss usually occurs due to milling of the test material between the upper and lower rings 38, 72. The 0.75 mm gap value was arrived at by trial-and-error for wheat flour and granulated sugar. The 0.75 mm gap prevented leakage of the test material, while providing a large enough gap to prevent test material particles from becoming entrapped between the upper and lower rings 38, 72. The CCSC 10 can operate at any specified gap setting from full contact to no contact by the upper and lower rings 38, 72.

Figure 7:
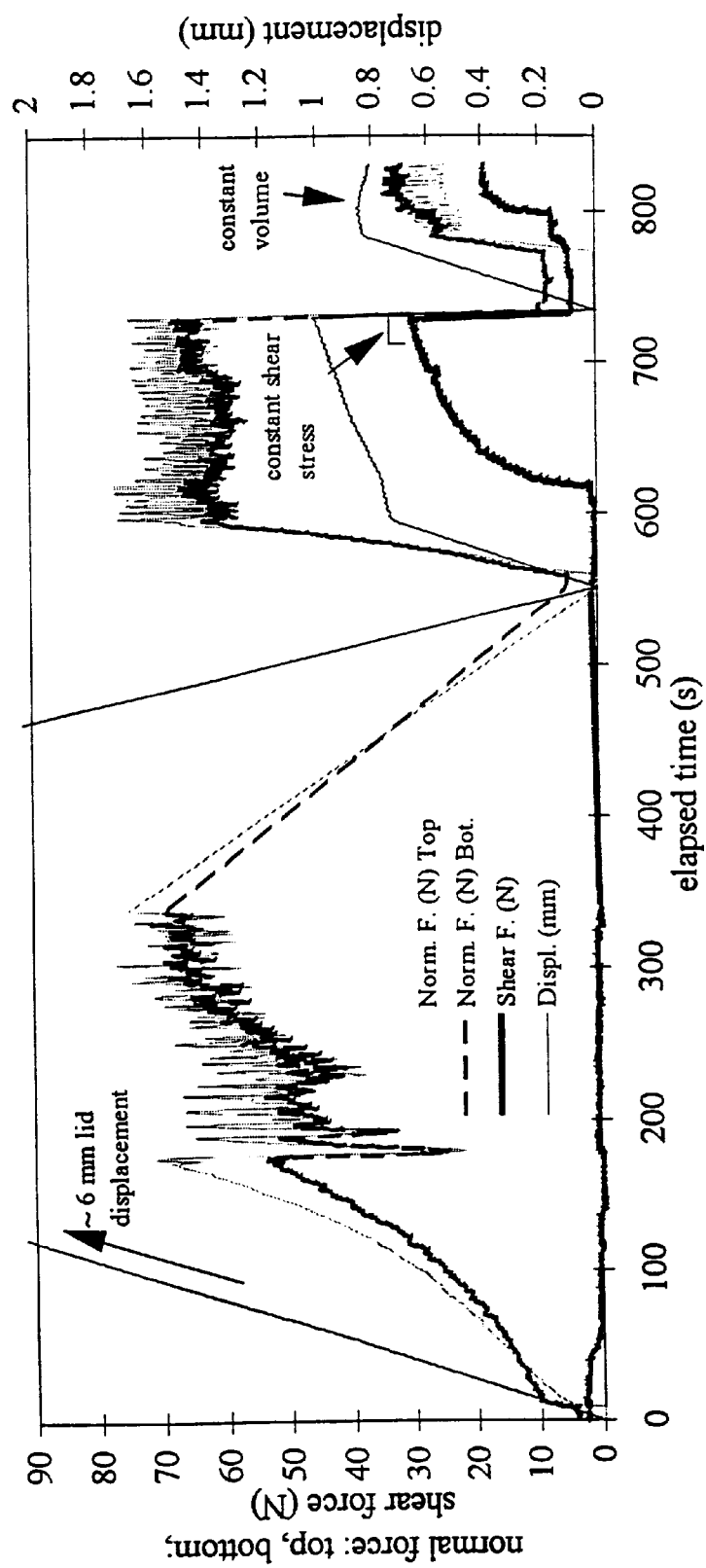
FIG. 7 is plot of recorded output data from the CCSC when used as a Jenike shear cell for wheat flour according to the present invention.
Figure 8:
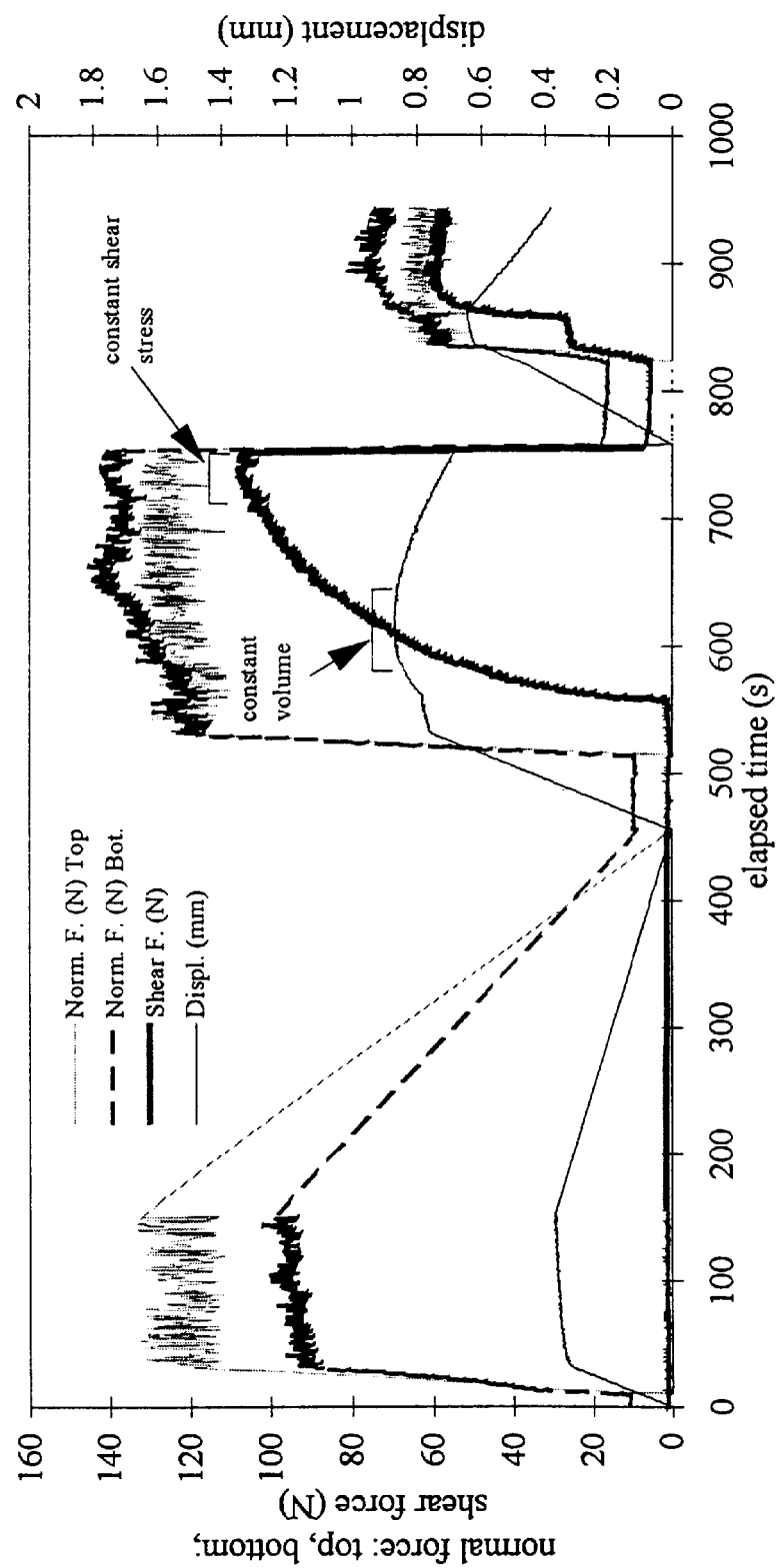
FIG. 8 is plot of recorded output data from the CCSC when used as a Jenike shear cell for granulated sugar according to the present invention.

FIGS. 7 and 8 show typical data from the CCSC prototype used as Jenike shear cell for wheat flour and sugar, respectively, including data from sample preparation. The data generated by the CCSC includes: shear force and stress, normal force and stress at the top of the specimen, normal force and stress at the bottom of the specimen, and lid displacement over entire duration of test. The lid displacement data were recorded, whereby the recorded data is increasing or positive in the downward direction, i.e., with decrease in test material volume. Table 2 shows flow parameter values recorded from the CCSC when used as Jenike shear cell.

TABLE 2

Flow parameters using the CCSC as Jenike shear cell

| Material | Consolidation stress (kPa) | Flow parameters | | | |
|---|---|---|---|---|---|
|  |  | Cohesion, c (kPa) | | tan φ | |
|  |  | Value | 95% C.I. | Value | 95% C.I. |
| Wheat flour | 13.6 | 1.73 | 1.35, 2.11 | 0.33 | 0.28, 0.37 |
|  | 27.3 | 3.82 | 2.75, 4.89 | 0.26 | 0.20, 0.33 |
| Granulated sugar | 24.2 | 2.14 | 0*, 4.33 | 0.89 | 0.76, 1.06 |
|  | 30.9 | 1.31 | 0*, 3.86 | 1.00 | 0.86, 1.83 |

*Negative lower bound values of the confidence interval for c were set to zero since c cannot assume negative values.

Different load values were recorded by the upper and lower load cells and clearly elucidate the importance and effect of powder/cell wall interaction. The normal load experienced during shear failure is expected to be in between these two values.

In the conventional Jenike test it is published that the rate of change of shear stress is monitored and critical state is assumed when the rate of change of shear stress is zero, i.e., when shear stress has stopped increasing. However, by definition, critical state is achieved when the test material's volume, and not shear stress, remains constant. The computer system controlled Jenike test data shows that constant material volume and constant shear are obtained at different stages of the test. As shown in FIG. 7 for the wheat flour, obtaining constant volume generally did not occur during the duration of a normal Jenike test. As shown in FIG. 8 for the granulated sugar, obtaining of constant volume occurred early during pre-shear. Whereby, the sugar was first reduced in volume briefly before maintaining constant volume, then dilating at an uninterrupted rate, even when the shear stress value leveled out.

The "steady state" and "yield" points used in determining yield loci during testing of the prototype were obtained by the conventional procedure of using the shear stress value where shear stress stopped for "steady state" point and using the first peak during shear to be the "yield" point. In the yield loci obtained by Kamath et al. using the conventional Jenike procedure, the "yield" points selected were the points at which the shear stress values had leveled off after initial yield, i.e., at "post yield steady state". This may account for lower cohesion and tan φ values listed in Table 2 for granulated sugar as compared to the values as given in Kamath, et al.. For example, the Kamath et al.'s values for the consolidation stress of 24.2 kPa, cohesion was 0.60 kPa and tan φ was 0.65, as compared to cohesion of 2.14 kPa and tan φ of 0.89 shown in Table 2. The cohesion and tan φ values measured for wheat flour using the CCSC as Jenike shear cell are within the 95% confidence interval of the reported values in Kamath et al.. The agreement in values for wheat flour may be attributed, again, to the post yield response of wheat flour as will be discussed further.

When the CCSC prototype was tested using with the described four stages of single test procedure, the reduction of normal load and rate of consolidation under shear was changed by allowing the lid 32 to lift as the test material dilated. This was accomplished by lifting the UTM crosshead at a constant rate during shearing. All tests were carried out for shearing at a lower ring displacement speed of 1 mm/min. The rate at which the cross-head was raised was estimated based on the rate of change of lid displacement from computer system controlled Jenike test data. Considerations for the displacement rate of the lid 32 included providing sufficient time for the test to run to allow steady change of conditions in the cell and allow adequate data collection; and the ability to complete the test before the limit of lower ring travel had been reached.

Figure 9:
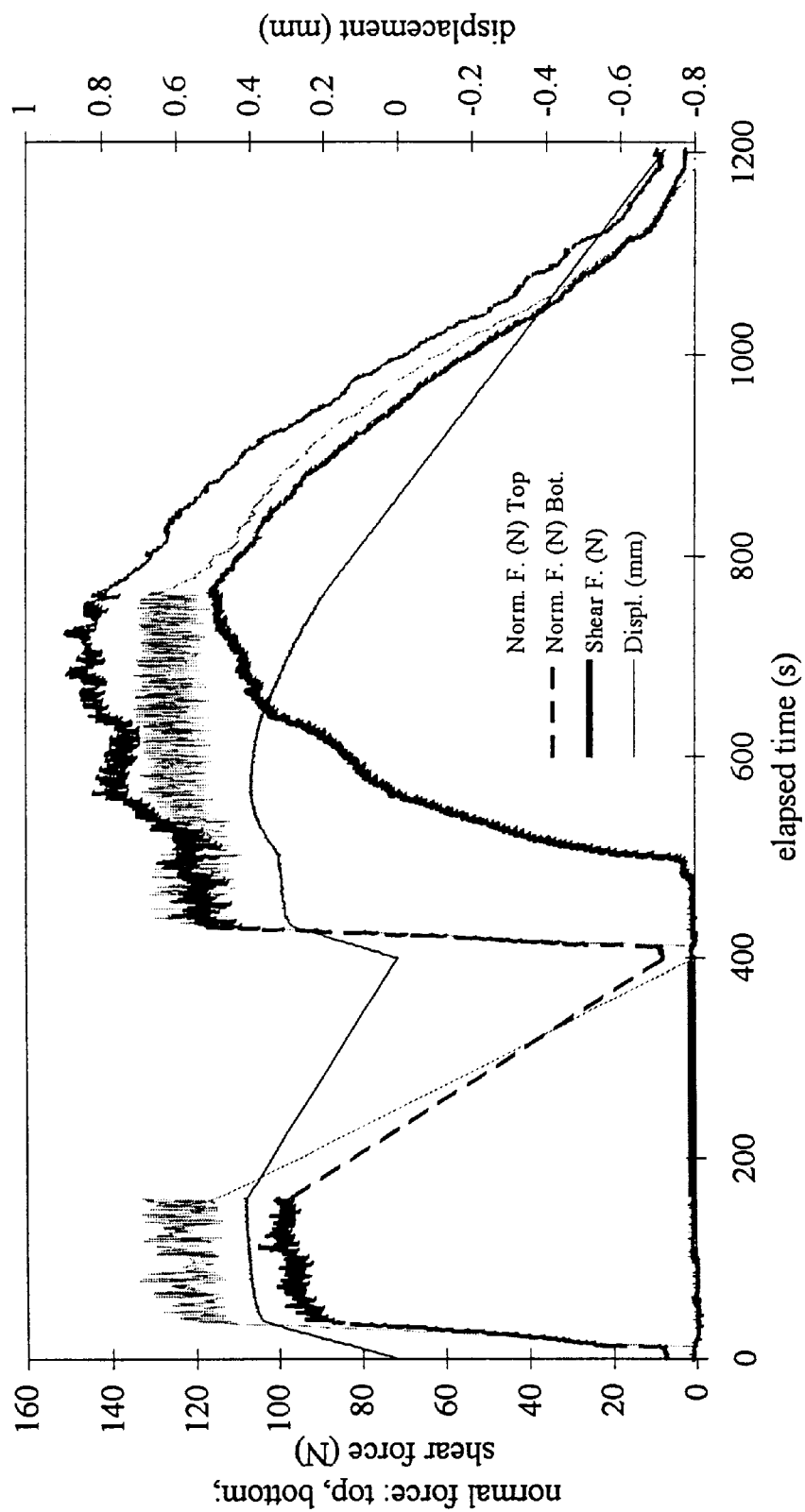
FIG. 9 is plot of recorded output data from the CCSC using a single test procedure for wheat flour according to the present invention.
Figure 10:
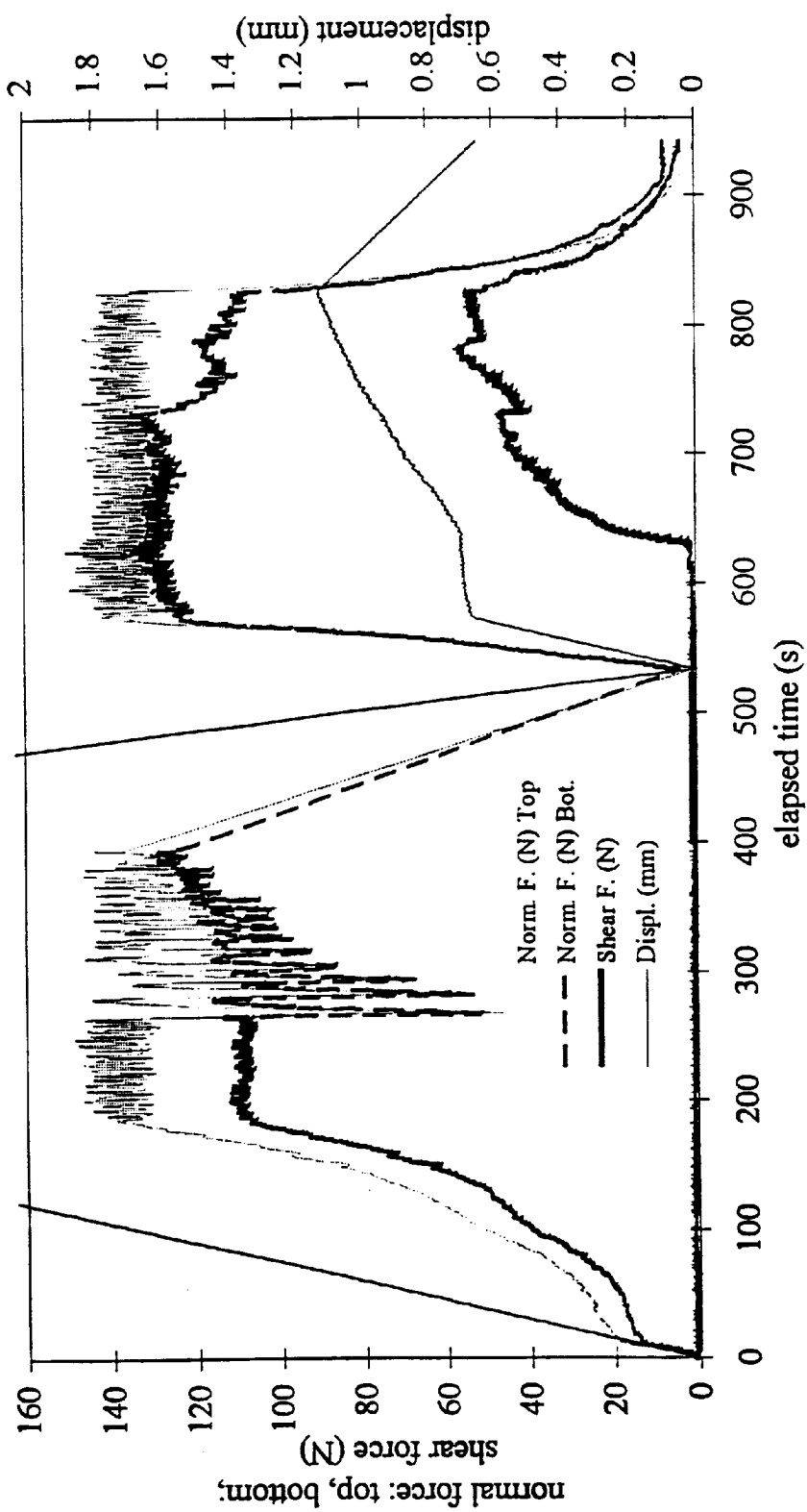
FIG. 10 is plot of recorded output data from the CCSC using a single test procedure for granulated sugar according to the present invention.
Figure 11:
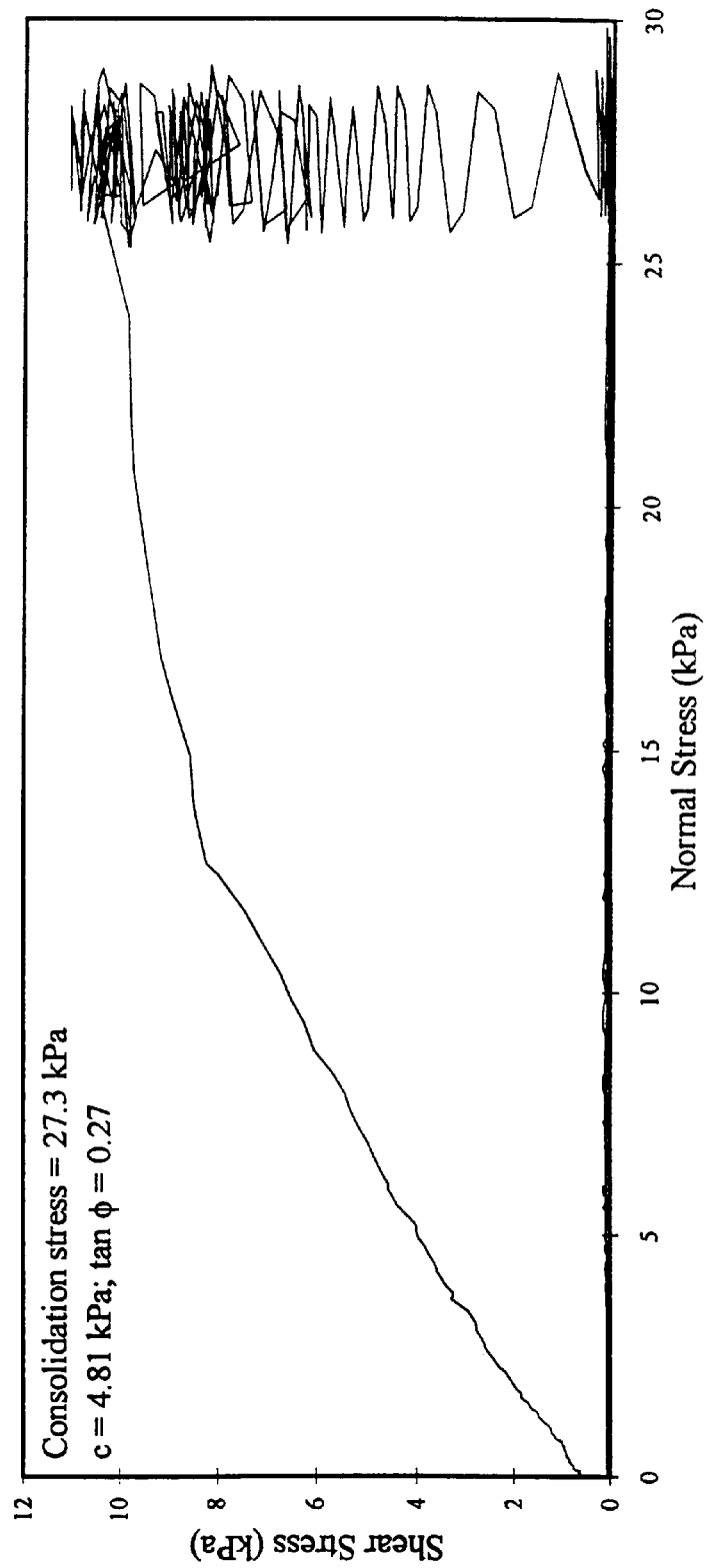
FIG. 11 is Yield Locus curve plot using the single test procedure for wheat flour according to the present invention.
Figure 12:
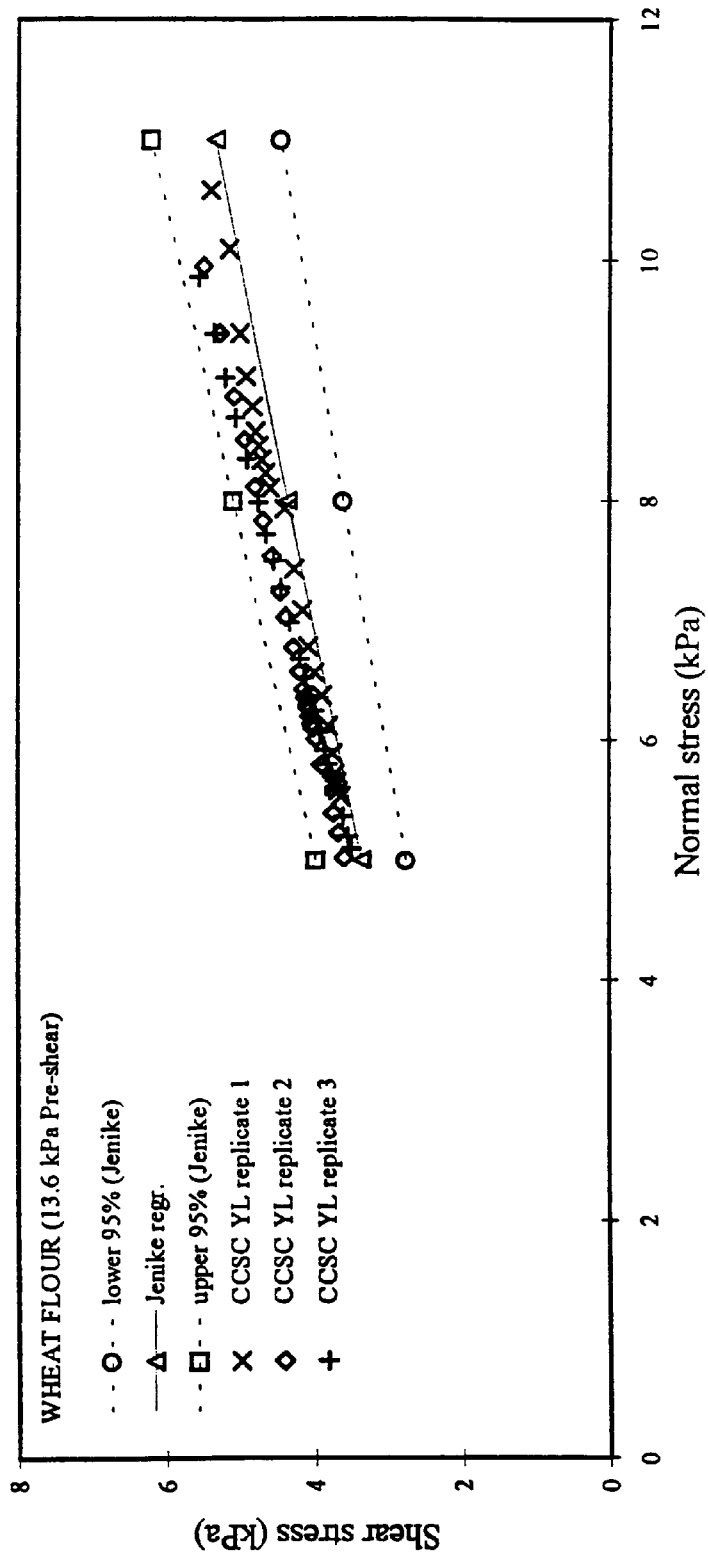
FIG. 12 is plot of recorded output data from the CCSC using the single test procedure and Jenike test procedure for wheat flour at a preshear consolidation load of 13.6 kPa according to the present invention.
Figure 13:
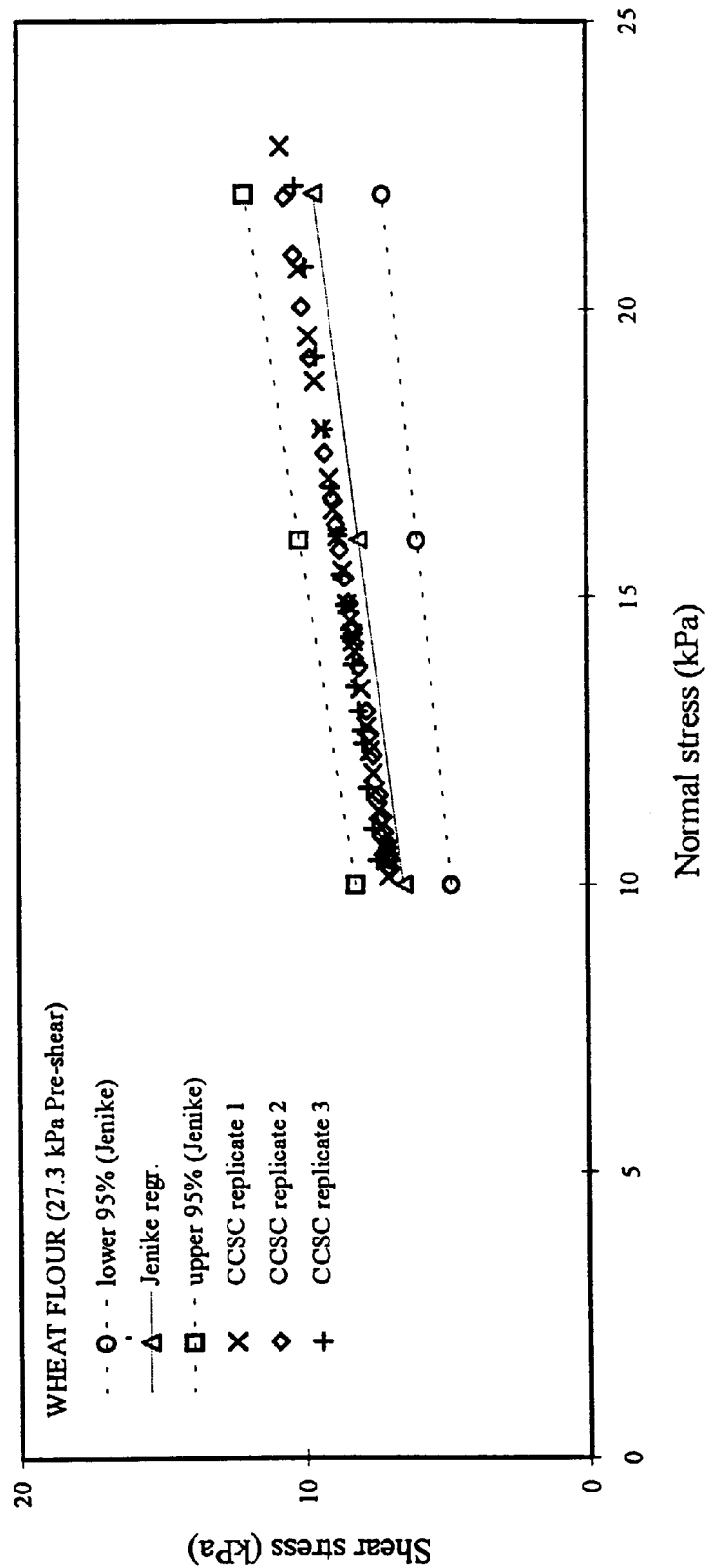
FIG. 13 is plot of recorded output data from the CCSC using the single test procedure and Jenike test procedure for wheat flour at a preshear consolidation load of 27.2 kPa according to the present invention.

FIGS. 9 and 10 show typical data from the single test procedure using the CCSC prototype for wheat flour and sugar, respectively. A typical Yield Locus curve obtained from the data for wheat flour (granulated sugar had similar response) is shown in FIG. 11. The cohesion and tan φ values were obtained by regressing the Yield Locus data in the same range as was used in the corresponding Jenike Yield loci determinations of Table 2. These ranges were 5.0 to 13.6 kPa and 10.0 to 27.3 kPa for wheat flour, and 7.8 to 24.2 kPa and 11.8 to 30.9 kPa for granulated sugar. Cohesion and tan φ values from the CCSC using the single test procedure and as Jenike shear cell are given in Table 3.

TABLE 3

Flow parameters measured using the CCSC-YLT and CCSC-Jenike apparatuses

| Material | Consolidation stress c(kPa) | Flow parameters | | | |
|---|---|---|---|---|---|
| | | CCSC-Jenike | | CCSC-YLT | |
| | | c (kPa) | tan φ | c (kPa) | tan φ |
| Wheat flour | 13.6 | 1.73 | 0.33 | 1.44 | 0.40 |
| | 27.3 | 3.82 | 0.26 | 4.10 | 0.29 |
| Granulated sugar | 24.2 | 2.14 | 0.89 | 0.00 | 0.93 |
| | 30.9 | 1.31 | 1.00 | 0.00 | 0.93 |

Figure 14:
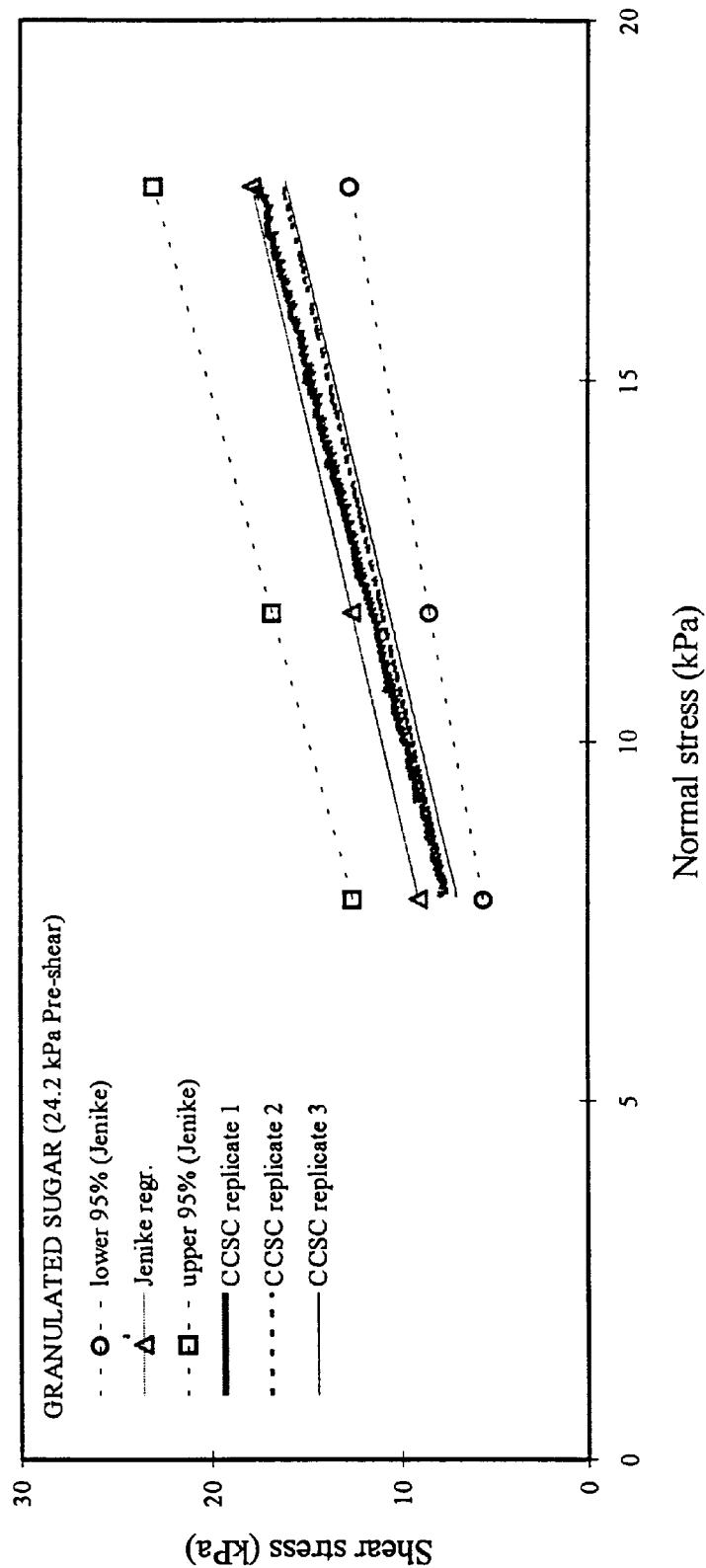
FIG. 14 is plot of recorded output data from the CCSC using the single test procedure and Jenike test procedure for granulated sugar at a preshear consolidation load of 24.2 kPa according to the present invention.
Figure 15:
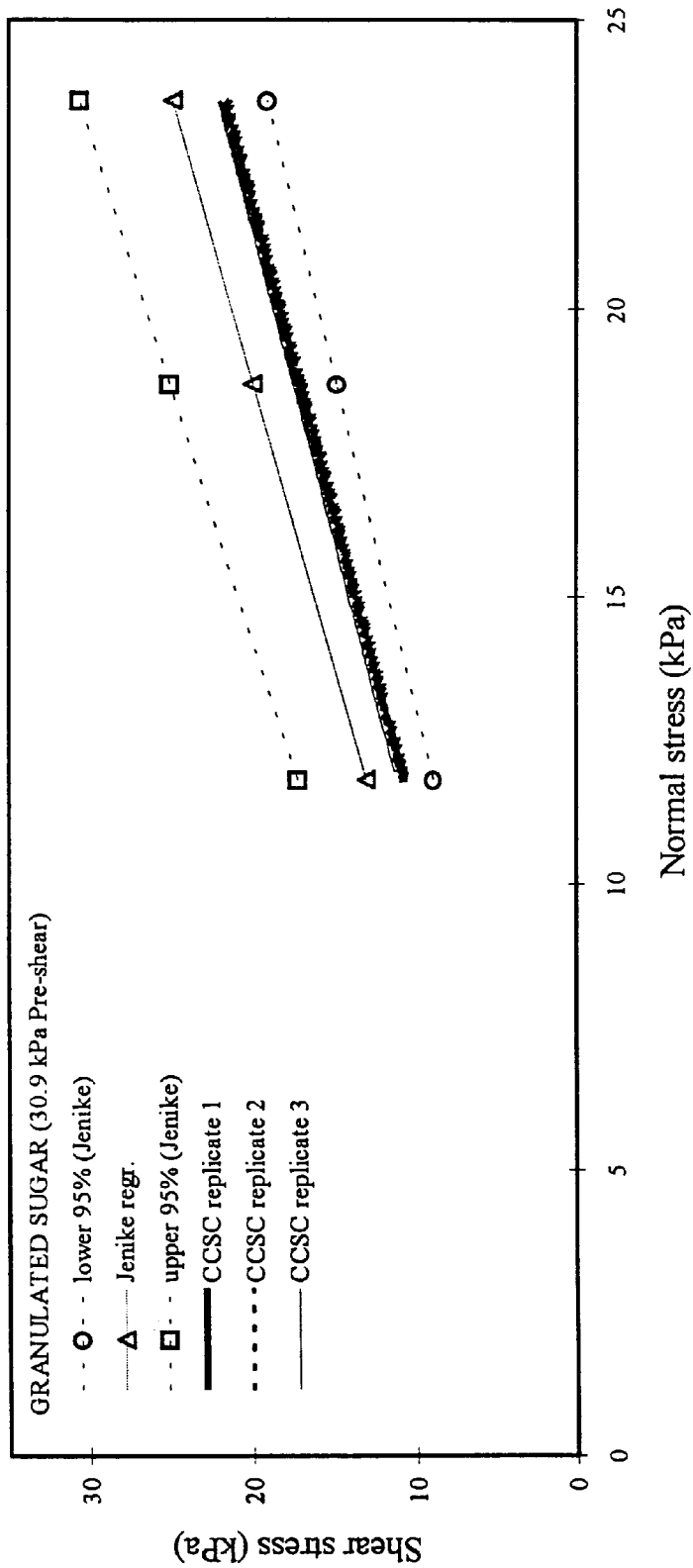
FIG. 15 is plot of recorded output data from the CCSC using the single test procedure and Jenike test procedure for wheat flour at a preshear consolidation load of 30.9 kPa according to the present invention.
Figure 16:
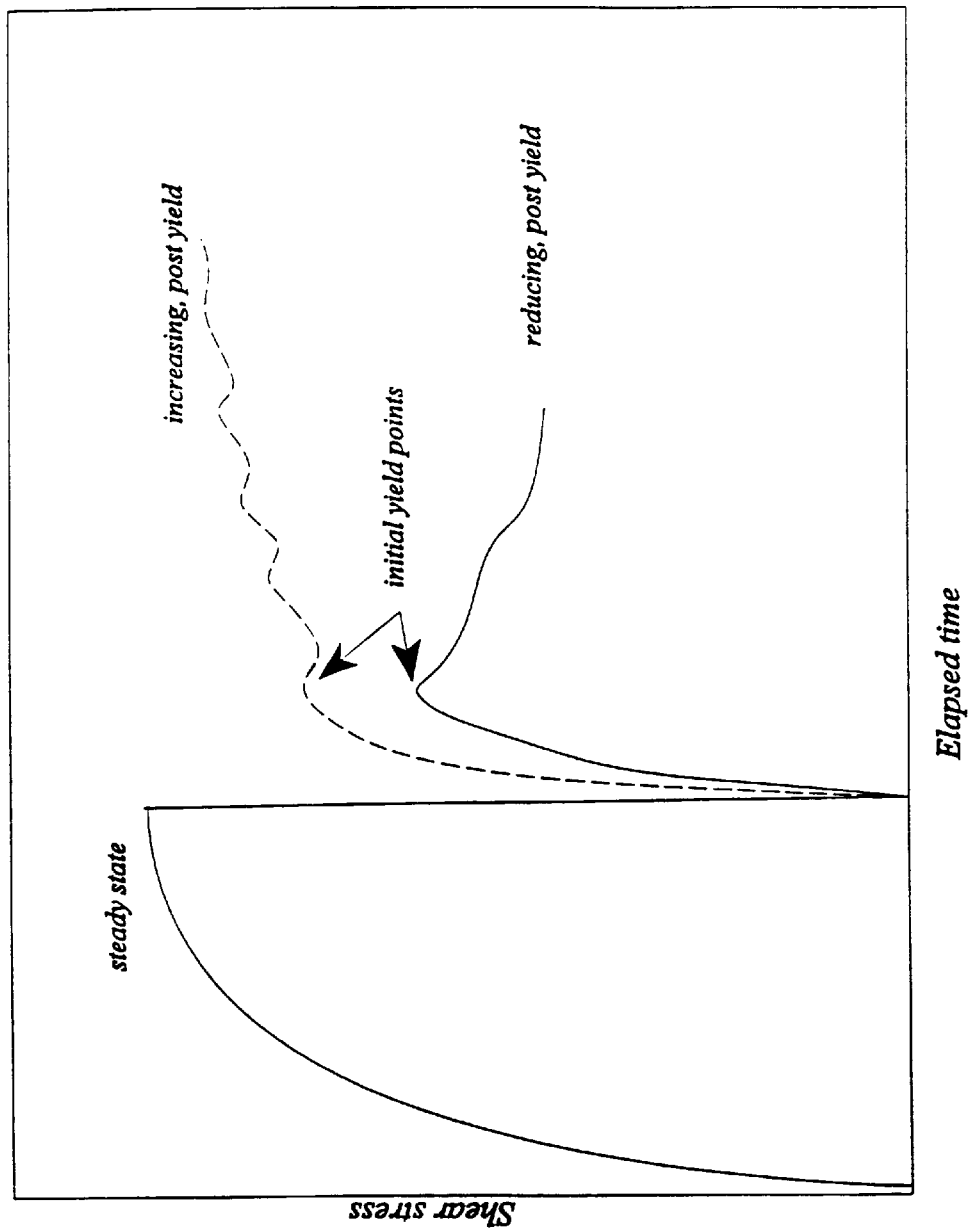
FIG. 16 is plot of general post yield states using the Jenike shear cell.
Figure 17:
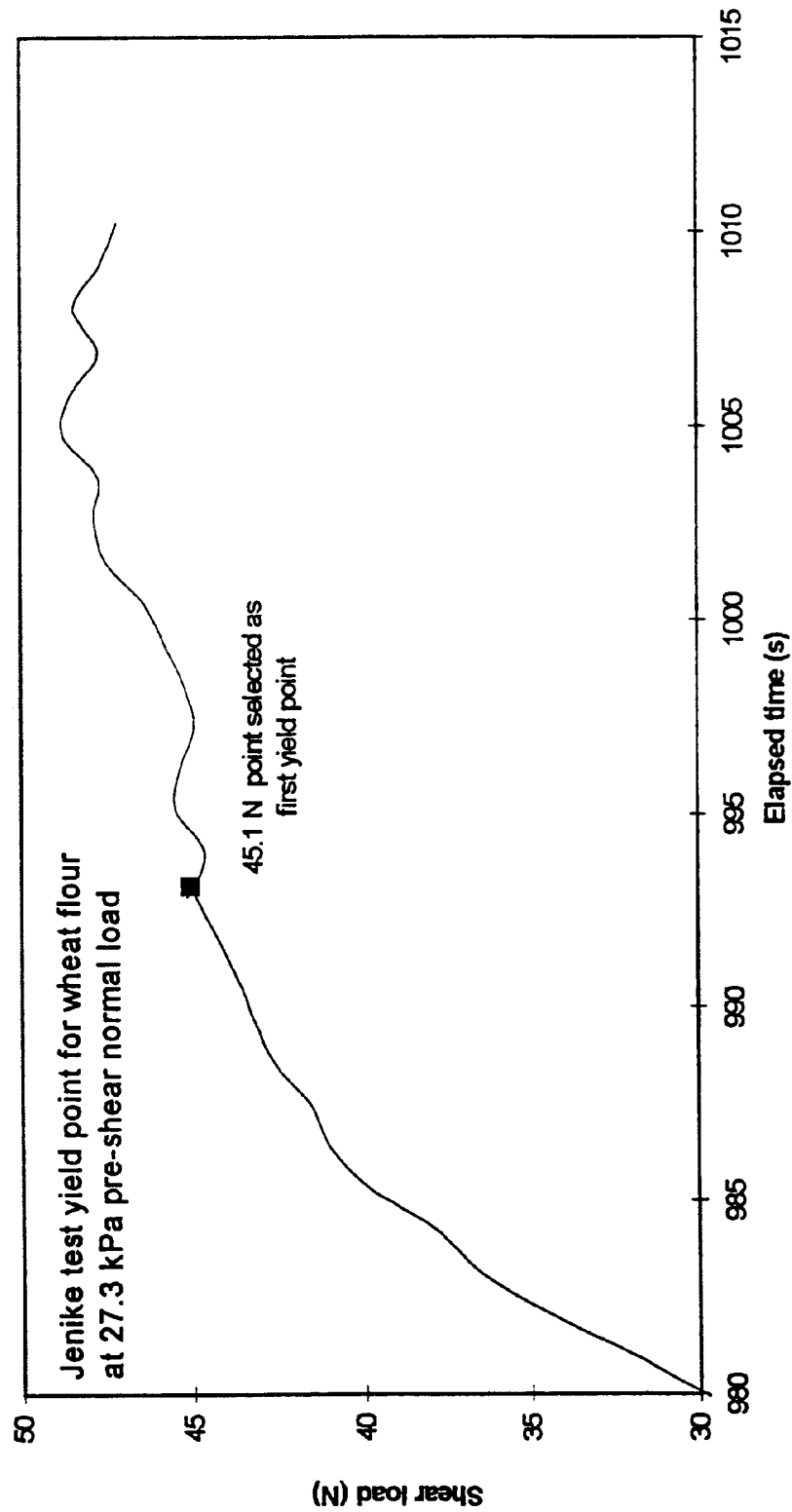
FIG. 17 is plot of post yield states for wheat flour using the Jenike shear cell.
Figure 18:
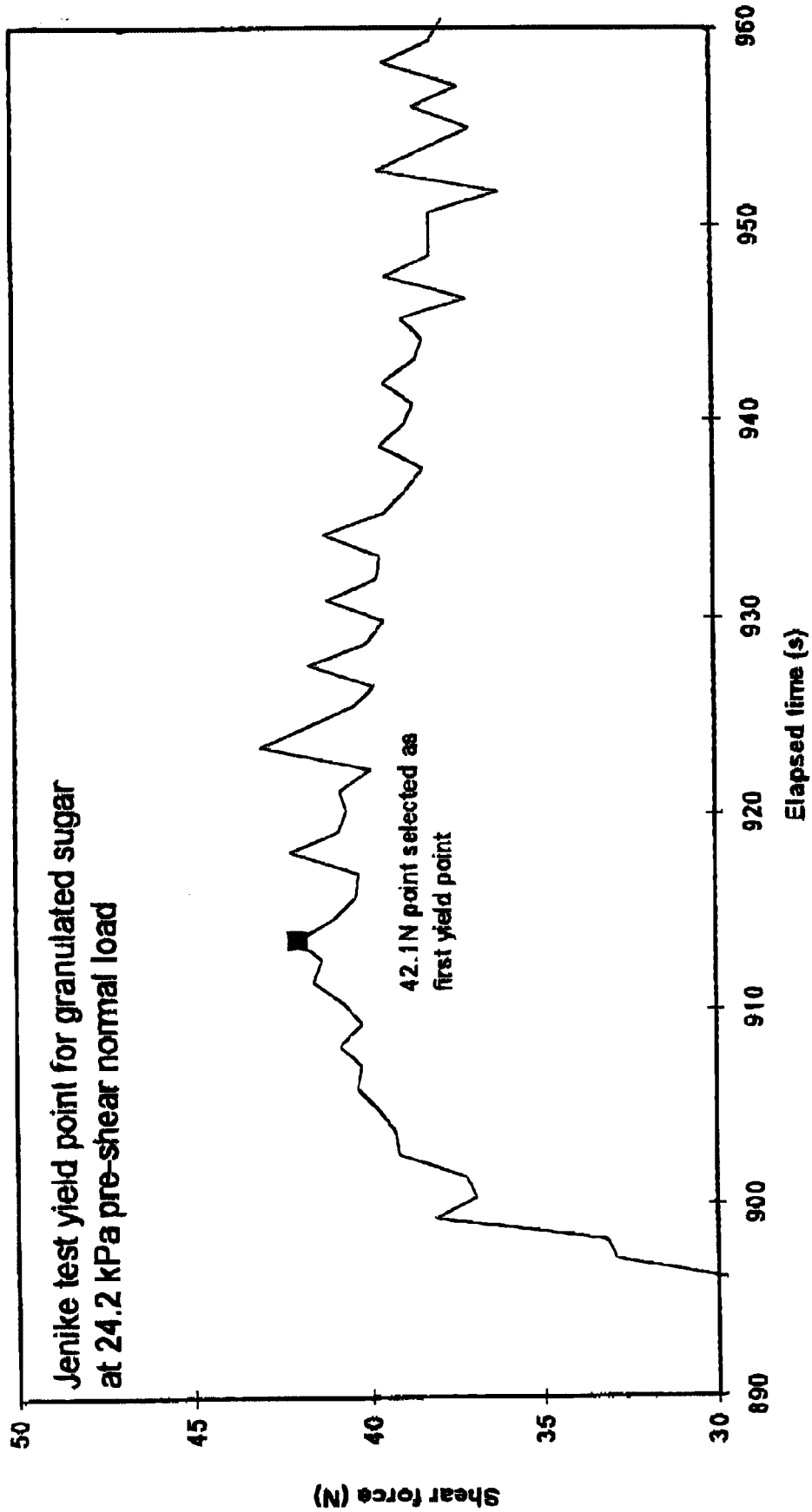
FIG. 18 is plot of post yield states for granulated sugar using the Jenike shear cell.

FIGS. 12 to 15 show the regressed yield loci from three replications obtained by using the single test procedure and CCSC prototype. The yield loci for the single test procedure are above the Jenike test procedure yield loci for wheat flour (FIGS. 12 and 13), and below for granulated sugar (FIGS. 14 and 15). The key to these differences may lie in the fact that the single test procedure data are a series of yield states, with varying normal and shear stresses, in the same test. This means that the yield point data being used to plot the yield loci are not the same as the initial yield points used in Jenike yield loci. The Jenike test is usually terminated after the initial yield point has been determined. If the test were allowed to continue, as illustrated in FIG. 16, the post yield behavior of the test material may show a reduction or increase in measured shear stress. FIG. 17 shows the post yield behavior of wheat flour, with post yield shear stress values higher than the initial yield point selected for the Jenike Yield Locus plot. This is a plausible explanation for the agreement between Kamath et al.'s flow parameter values for wheat flour with the CCSC single test procedure values shown in Table 2. Similarly, FIG. 18 shows post yield behavior of granulated sugar, showing post yield values lower than the selected initial yield point using the CCSC-Jenike test procedure. This explains lower values of flow parameter values for the granulated sugar than reported in Kamath et al.. Post yield trends shown in FIGS. 16–18 are consistent with the data shown in the plots of FIGS. 12–15 for the CCSC-single test procedure and the CCSC-Jenike teat procedure.

Different rates of lift (from 0.125 to 0.0250 mm/min) were used to determine the optimum rate of lift for the lid of the prototype during the single test procedure when the load was reduced. Inspection of results suggested that changing the rate of cross-head lift had no noticeable effect, provided the contact by the lid with the material was maintained and the material was not over consolidated. The tests with wheat flour and granulated sugar revealed that the CCSC-single test procedure required less than ¼ of the time to generate equivalent data with the CCSC used as a Jenike shear cell. In addition, the amount of material needed for testing was ⅓ of material used the Jenike testing procedure was used. The values of ¼ the time and ⅓ the material are the mean of the tests conducted.

Statistical comparisons for flow parameters of the CCSC-single test procedure and CCSC-Jenike procedure are shown in Table 4.

TABLE 4

Comparison of flow parameters obtained by the CCSC-YLT and the CCSC-Jenike tests

| Material | Consolidation stress (kPa) | Flow property | Null hypothesis ($H_0$) Test method comparison | F* | F ($\alpha$ = .05) | Significant difference |
|---|---|---|---|---|---|---|
| Wheat flour | 13.6 | c | CCSC-Jenike = CCSC-YLT | 0.438 | 3.92 | NO |
| Wheat flour | 13.6 | tan $\phi$ | CCSC-Jenike = CCSC-YLT | 3.50 | 3.92 | NO |
| Wheat flour | 27.3 | c | CCSC-Jenike = CCSC-YLT | 0.352 | 4.00 | NO |
| Wheat flour | 27.3 | tan $\phi$ | CCSC-Jenike = CCSC-YLT | 0.130 | 4.00 | NO |
| Granulated sugar | 24.2 | c | CCSC-Jenike = CCSC-YLT | 4.67 | 3.84 | YES |
| Granulated sugar | 24.2 | tan $\phi$ | CCSC-Jenike = CCSC-YLT | 0.00 | 3.84 | NO |
| Granulated sugar | 30.9 | c | CCSC-Jenike = CCSC-YLT | 5.00 | 3.84 | YES |
| Granulated sugar | 30.9 | tan $\phi$ | CCSC-Jenike = CCSC-YLT | 18.0 | 3.84 | YES |

For the wheat flour, there were no differences between the testers within a 95% confidence interval for either of the consolidation stresses. However, for the less cohesive material of granulated sugar, there were significant differences. At the consolidation stress value of 24.2 kPa for the sugar, tan $\phi$ was not significantly different but the cohesion (c) values, although significantly different, had marginally different F-statistic (F*=4.67 vs. F($\alpha$=0.05)=3.84). There was a similar marginal difference (F*=5.00 vs. F($\alpha$=0.05)=3.84) between cohesion values at 30.9 kPa of consolidation stress. The only major difference (F*=18.0 vs. F($\alpha$=0.05)=3.84) was in tan $\phi$ for granulated sugar at 30.9 kPa consolidation stress (0.93 vs. 1.00). This may be attributed to post yield behavior as discussed in the preceding subsection. The data obtained both using the CCSC-single test procedure and CCSC-Jenike were compared to the published flow parameters Akers, R. J., *The certification of a limestone powder for Jenike testing*: CRM 116. Bureau of Common Reference (BCR), Commission of the European Communities, Luxembourg, 1992. At the 0.05 level of significance there were only marginal differences in cohesion and angle of internal friction values between the BCR published data, CCSC-single test procedure and CCSC-Jenike procedure shear cell values.

The CCSC prototype successfully produced yield loci from a single test. In addition, by selecting different options in the computer program, the CCSC could also be used as a Jenike shear cell or a direct shear cell. Where the direct shear cell is the same as the Jenike, but with out the twisting of the lid or consolidation of the test material. Testing showed that there were no significant differences in the yield loci results between the CCSC-Jenike shear cell and the CCSC-single test procedure for the fine cohesive material of wheat flour, while there were marginal differences for a granular, less cohesive material of sugar. Also, the CCSC eliminated the need for trial-and-error in determining the number of twists needed for critical consolidation, thereby reducing operator error. In addition, the duration of the test and amount of material needed to generate a data using the CCSC-single test procedure are reduced as compared to tests of the CCSC used as a Jenike shear cell. Use of the CCSC with testing either testing procedure minimizes the effects of operator error by allowing consistent consolidation, without the need for trial-and-error in determining the required number of twists for consolidation in Jenike-type shear tests. It also aids in eliminating error introduced by ring-to-ring contact during shearing by maintaining any specified gap between upper and lower rings.

We claim:

1. A shear cell for measuring shear properties of a material comprising:
   a lower measuring device for measuring load;
   a movable ring platform connected to and movable along said lower measuring device;
   a lower ring mounted to an upper surface of said movable ring platform;
   a fixed ring platform supported above said lower ring and movable ring platform;
   an upper ring mounted to a lower surface of said fixed ring platform and above said lower ring;
   a lid;
   a lid opening in said fixed ring platform to allow access to said upper ring;
   a lid movement apparatus connected to said lid to move said lid and apply a load to said lid;
   an upper measuring device connected to said lid movement device to measure the load applied to said lid;
   an actuator connected to said movable ring platform for moving said movable ring platform along said lower measuring device; and
   an actuator measuring device connected to said actuator to measure load experienced by the actuator during movement of said movable ring platform.

2. The shear cell of claim 1, further including an indexer connected to said actuator for controlling movement of said actuator.

3. The shear cell of claim 1, further including a computer to receive load data from said upper, lower and actuator measuring devices and to control movement of said actuator and lid movement apparatus.

4. The shear cell of claim 1, further including a molding ring connectable to said upper ring through said lid opening.

5. The shear cell of claim 1, wherein said lid movement apparatus allows twisting of the lid by hand.

6. The shear cell of claim 1, further including a framework of supports to secure components of the shear cell, said framework including a base to support said lower measuring device; and at least one upright support extending upward from said base to support said fixed ring platform at a height above said movable ring platform and said lower measuring device.

7. The shear cell of claim 6, further including an actuator base mounted near said framework so that said actuator can be connected to said movable ring platform.

8. The shear cell of claim 6, wherein said height of said fixed ring platform above said movable ring platform is adjustable.

9. The shear cell of claim 6, further including a threaded stud adjustably extending from each upright support to support said fixed ring platform; at least two lock down latch supports mounted to said frame work; a lock down latch attached to each of said lock down latch supports; and at least two catches attached to said fixed ring platform for securing said fixed ring platform to said studs using said lock down latches.

10. The shear cell of claim 1, wherein said upper, lower and actuator measuring devices are load cells.

11. The shear cell tester of claim 1, wherein said lid movement apparatus allows twisting of said lid.

12. A shear cell for measuring shear properties of a material comprising:

a lower measuring means for measuring load;

a movable ring platform means connected to and movable along said lower measuring means;

a lower ring means mounted to said movable ring platform means;

a fixed ring platform means supported above said lower ring means and movable ring platform means;

an upper ring means mounted to said fixed ring platform means and above said lower ring means;

a lid means;

a lid opening in said fixed ring platform means to allow access to said upper ring means;

a lid movement means connected to said lid means for moving said lid means and applying a load to said lid means;

an upper measuring means connected to said lid movement means to measure the load applied to said lid means;

an actuator means connected to said movable ring platform means for moving said movable ring platform means along said lower measuring means; and an actuator measuring means connected to said actuator means to measure load experienced by said actuator means during movement of said movable ring platform means.

13. The shear cell tester of claim 12, further including a computer means to control said tester and record data from said upper, lower and actuator measuring means.

14. A shear test procedure for generating a Yield Locus plot comprising:

a. aligning an upper ring with a lower ring to form a shear cell;

b. loading a test material into the shear cell;

c. placing a lid into said upper ring to initially consolidate the test material;

d. twisting the lid while applying a normal load to the lid until the test material is critically consolidated;

e. displacing the lower ring in relationship to the upper ring while applying the normal load to the lid;

f. measuring the load due to shear stress of the material as the lower ring is displaced;

g. displacing the lower ring until a steady state failure condition is reached, said steady state failure marked by shear stress $T_{pr}$, remaining constant;

h. decreasing the normal load slowly after the steady state failure condition has been reached; and i. continuously recording normal load values and shear stress values of the test material as the normal load is reduced.

15. The shear test procedure of claim 14, further including plotting shear stress values vs. normal load.

16. The shear test procedure of claim 14, further including layering the test material into the cell by sprinkling to increase the consolidation of the test material.

17. The shear test procedure of claim 14, further including using a molding ring with the shear cell.

18. The shear test procedure of claim 14, using a programmed computer to control movement of the lid; applying the load to the lid; displacing the lower ring; measuring of the shear stress of the material; decreasing the normal load; and recording values of shear stress and normal load.

19. The shear test procedure of claim 14, wherein step h the lid is allowed to lift as the test material dilates.

20. The shear test procedure of claim 14, wherein step h is replaced by stopping displacement of the lower ring; removing the normal load associated with the lid; choosing a second normal load less than the normal load value at the steady state failure condition; applying the second normal load to the lid; continuing displacement of the lower ring until a maximum shear stress value is reached; and recording the maximum shear stress value.

21. The shear test procedure of claim 20, wherein the process of applying the normal load to the lid includes cycling of the lid up and down without losing lid contact with the test material to simulate a static load.

22. The shear test procedure of claim 20, using a programmed computer to control movement of the lid; applying the load to the lid; displacing the lower ring; measuring of the shear stress of the material; removing the normal load; applying a second normal load; and recording values of shear stress and normal load.

* * * * *

UNITED STATES PATENT AND TRADEMARK OFFICE
CERTIFICATE OF CORRECTION

| | |
|---|---|
| PATENT NO. | : 6,003,382 |
| APPLICATION NO. | : 09/104650 |
| DATED | : December 21, 1999 |
| INVENTOR(S) | : Virendra M. Puri et al. |

It is certified that error appears in the above-identified patent and that said Letters Patent is hereby corrected as shown below:

Col. 1 lines 6-7 should read

STATEMENT OF GOVERNMENT SPONSORSHIP

This invention was made with government support under Hatch Act Project No. PEN03488, awarded by USDA. The Government has certain rights in the invention.

Signed and Sealed this

Third Day of November, 2009

David J. Kappos
*Director of the United States Patent and Trademark Office*